United States Patent
Oki et al.

(10) Patent No.: US 12,140,515 B2
(45) Date of Patent: Nov. 12, 2024

(54) CORROSION EVALUATION SUPPORT APPARATUS AND CORROSION EVALUATION SUPPORT METHOD

(71) Applicant: Nippon Telegraph and Telephone Corporation, Tokyo (JP)

(72) Inventors: Shota Oki, Musashino (JP); Shingo Mineta, Musashino (JP); Mamoru Mizunuma, Musashino (JP); Masayuki Tsuda, Musashino (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 405 days.

(21) Appl. No.: 17/607,783

(22) PCT Filed: May 20, 2019

(86) PCT No.: PCT/JP2019/019888
§ 371 (c)(1),
(2) Date: Oct. 29, 2021

(87) PCT Pub. No.: WO2020/234958
PCT Pub. Date: Nov. 26, 2020

(65) Prior Publication Data
US 2022/0221387 A1    Jul. 14, 2022

(51) Int. Cl.
*G01N 11/00* (2006.01)
*G01N 17/02* (2006.01)
*G01N 33/24* (2006.01)

(52) U.S. Cl.
CPC ............. *G01N 11/00* (2013.01); *G01N 33/24* (2013.01); *G01N 17/02* (2013.01)

(58) Field of Classification Search
CPC ...................................................... G01N 11/00
See application file for complete search history.

(56) References Cited

U.S. PATENT DOCUMENTS

2021/0199561 A1*   7/2021   Oki ..................... G01N 33/24

OTHER PUBLICATIONS

Widjaja et al.; "Flow box test for viscosity of soil in plastic and viscous liquid states"; Soils and Foundations (2013); 53(1):35-46; Jan. 26, 2013 (Year: 2013).*
Chen et al.; "Measurement of the viscosity coefficient of liquefied silty soil"; Geo-Marine Letters (2019) 39:135â148; Apr. 10, 2019 (Year: 2019).*
M. Barbalat et al., *Electrochemical Study of the Corrosion Rate of Carbon Steel in Soil: Evolution with Time and Determination of Residual Corrosion Rates Under Cathodic Protection*, Corrosion Science, vol. 55, 2012, pp. 246-253.

* cited by examiner

*Primary Examiner* — Ryan D Walsh
(74) *Attorney, Agent, or Firm* — Workman Nydegger

(57) ABSTRACT

An object is to support evaluation of corrosion of metal embedded in the ground such that the corrosion can be evaluated with high accuracy even if any type of soil is used. A coarseness/fineness test unit analyzes soil particles of soil that is used to evaluate corrosion of an embedded metallic material, a water supply unit supplies water to the soil, a soil stirring unit stirs the soil supplied with water, and a viscosity test unit measures fluidity of the stirred soil.

14 Claims, 6 Drawing Sheets

CORROSION EVALUATION SUPPORT APPARATUS AND CORROSION EVALUATION SUPPORT METHOD

TECHNICAL FIELD

The present invention relates to a technology for evaluating corrosion of a metallic material that is embedded in the ground.

BACKGROUND ART

In recent years, accidents that are caused due to deterioration of infrastructure equipment frequently occur worldwide, and are serious social problems. Examples of such accidents include the collapse of the Silver Bridge in the U.S. in 1967, the collapse of the Sasago Tunnel in Japan in 2012, and the collapse of the Morandi Bridge in Italy in 2018. A large number of such infrastructure equipment was rapidly installed in about 20 years from the period of rapid economic growth, and it is said that in 2030, 50 years will pass from the construction of more than half such equipment.

Accordingly, there is a concern that more and more equipment will deteriorate in the future, and serious accidents like those described above will frequently occur in the future. Therefore, it is necessary to shift an operation method of infrastructure management from conventional post-maintenance in which measures are taken after the occurrence of breakdown to preventive maintenance in which measures are taken before the occurrence of breakdown by predicting deterioration of equipment by some means, for example.

One of important factors for realizing preventive maintenance is how to predict deterioration. A common method for predicting deterioration is a statistical method. A statistical method is characterized in that a regularity that underlies a deterioration process is modeled using a huge amount of inspection data of equipment, and an average deterioration phenomenon of all equipment can be grasped.

CITATION LIST

Non Patent Literature

[NPL 1] M. Barbalat, L. Lanarde, D. Caron, M. Meyer, J. Vittonato, F. Castillon, S. Fontaine, Ph. Refait, "Electrochemical study of the corrosion rate of carbon steel in soil: Evolution with time and determination of residual corrosion rates under cathodic protection", Corrosion Science 55 (2012) 246-253.

SUMMARY OF THE INVENTION

Technical Problem

In the case of imaginary equipment of which abundant inspection data is accumulated through daily inspections, it is effective to predict deterioration using the statistical method. However, equipment that is embedded in the ground cannot be directly seen, and therefore inspection data cannot be easily obtained, and in most cases, data that is sufficient for statistical analysis is not accumulated.

Examples of equipment embedded in the ground include water-supply pipelines, gas-supply pipelines, pipelines for power cables, underground tanks, overpacking materials of spent nuclear fuel, steel-pipe columns, and branch line anchors, and metallic materials such as steel materials are used in numerous cases. Deterioration of a metallic material that is embedded in the ground progresses due to soil corrosion. Soil corrosion is a phenomenon in which the thickness of a member decreases with rust forming on an interface at which the metallic material is in contact with soil.

In order to predict deterioration of equipment embedded in the ground, it is effective to find out a corrosion mechanism from the viewpoint of the material, and establish a corrosion estimation formula. To realize this, it is necessary to evaluate the manner in which corrosion of a steel material in the ground proceeds. A plurality of methods are conceivable as methods for the evaluation.

A first method is a method of evaluating corrosion of existing outdoor equipment in a noninvasive manner. However, there are many inconveniences in outdoor evaluation, such as installation of required devices, establishment of a measurement system, and selection of a measurement target while avoiding city areas and the like, and it is envisaged that evaluation will be difficult if an underground structure has a complex shape.

A second method is an exposure test method in which a sample is embedded in an outdoor environment to evaluate corrosion. In this method, the shape, surface area, weight, thickness, and the like of the embedded sample can be specified in advance, and therefore the degree of progress of corrosion can be evaluated from an amount of change between before and after the exposure test. However, evaluation cannot be performed until the sample actually corrodes to such an extent that the corrosion can be visually observed, and therefore it takes a too long time, and this is a critical defect.

Therefore, it is thought that the most effective method is a third method in which a system is established indoors by simulating an actual environment and minute corrosion that progressed in a short period of time is electrochemically evaluated. The greatest merit is in that a large-scale experiment system can be easily established in an indoor environment, and it takes a short time until a result is obtained. In order to assure reliability of data that is obtained in an indoor experiment, it is important to confirm reproducibility by carrying out evaluation a plurality of times. For this purpose, an evaluation system needs to be established such that the experiment can be performed every time under the same conditions.

In the indoor experiment, soil is placed in a container and an electrode (evaluation sample) is embedded in the soil to perform electrochemical measurement. The electrochemical measurement is described in NPL 1, for example. One of important items that are to be considered when reproducing a simulated environment indoors is the state of the soil in the container. A corrosion rate is largely affected by the state of water and oxygen that are present on a metal surface. Therefore, in order to simulate diffusion behaviors of water and oxygen to the metal surface, it is important to pack soil into the container without forming a gap and to embed the electrode in such a manner that an interface between the metal surface and soil particles can be evaluated under the same conditions with good reproducibility.

Sandy soil that is constituted by relatively large soil particles is usually "smooth", and it is easy to pack sandy soil into the container and embed the electrode in sandy soil under the same conditions. However, it is difficult to embed the electrode in some types of soil. A representative example of such soil is sticky soil. Soil particles constituting sticky soil are as small as several micrometers, and therefore capillary pressure that acts in gaps between the particles is high, and adhesion between the particles is strong, and therefore sticky soil is usually "sticky". Therefore, it is difficult to pack sticky soil into the container without forming a gap. Also, in the case of sticky soil, it is difficult to control an interface between metal and soil particles to be under the same conditions, and there is a big concern from the viewpoint of assuring reproducibility of measurement data.

The present invention was made in view of the problems described above, and an object of the present invention is to provide a technology for supporting evaluation of corrosion of metal embedded in the ground such that the corrosion can be evaluated with high accuracy even if any type of soil is used.

Means for Solving the Problem

An aspect of the present invention is a corrosion evaluation support device including: a coarseness/fineness test unit configured to analyze soil particles of soil that is used to evaluate corrosion of an embedded metallic material; a water supply unit configured to supply water to the soil; a soil stirring unit configured to stir the soil supplied with water; and a viscosity test unit configured to measure fluidity of the stirred soil.

Another aspect of the present invention is a corrosion evaluation support method to be carried out by a corrosion evaluation support device, the method including: an analysis step of analyzing soil particles of soil that is used to evaluate corrosion of an embedded metallic material; a water supply step of supplying water to the soil; a stirring step of stirring the soil supplied with water; and a measurement step of measuring fluidity of the stirred soil.

Effects of the Invention

According to the present invention, it is possible to support evaluation of corrosion of metal embedded in the ground such that the corrosion can be evaluated with high accuracy even if any type of soil is used.

DESCRIPTION OF EMBODIMENTS

A soil environment is a complex environment in which three phases of a solid phase, a liquid phase, and a gas phase coexist. It is said that corrosion of a metallic material that is embedded in soil basically progresses based on reactions expressed by the following formulas (1) and (2) similarly to corrosion that occurs in the air and an aqueous solution.

$$Fe \rightarrow Fe^{2+} + 2e^- \qquad (1)$$

$$O_2 + 2H_2O + 4e^- \rightarrow 4OH^- \qquad (2)$$

The above formula (1) expresses a cathodic reaction through which the thickness of a member constituted by the metallic material decreases as a result of iron being ionized. The formula (2) expresses an anodic reaction in which dissolved oxygen in water accepts electrons and hydroxide ions are generated. From these formulas, it can be understood that the presence of water and oxygen on a metal surface is necessary for the progress of a corrosion reaction.

The principal characteristic of soil corrosion is in that soil particles are involved as a solid phase. In soil corrosion, there are various states of the metal surface, for example, there are a region where soil particles are in contact with the metal surface, a region where water is in contact with the metal surface, a region where water is entrapped due to a capillary phenomenon in a gap in the vicinity of a region where soil particles are in contact with the metal surface, and a region where air is in contact with the metal surface. That is, when evaluating soil corrosion in an indoor simulated environment, an evaluation system needs to be established such that the state of an interface between the metal surface and soil particles can be made the same every time an experiment is performed, to assure reproducibility. Therefore, embodiments of the present invention provide a corrosion evaluation support technology that makes it possible to measure corrosion of metal (steel material) embedded in the ground with good reproducibility even if any type of soil is used.

The following describes the embodiments of the present invention using the drawings. Note that portions that are common to a plurality of drawings are denoted with the same reference sign.

First Embodiment

Figure 1:
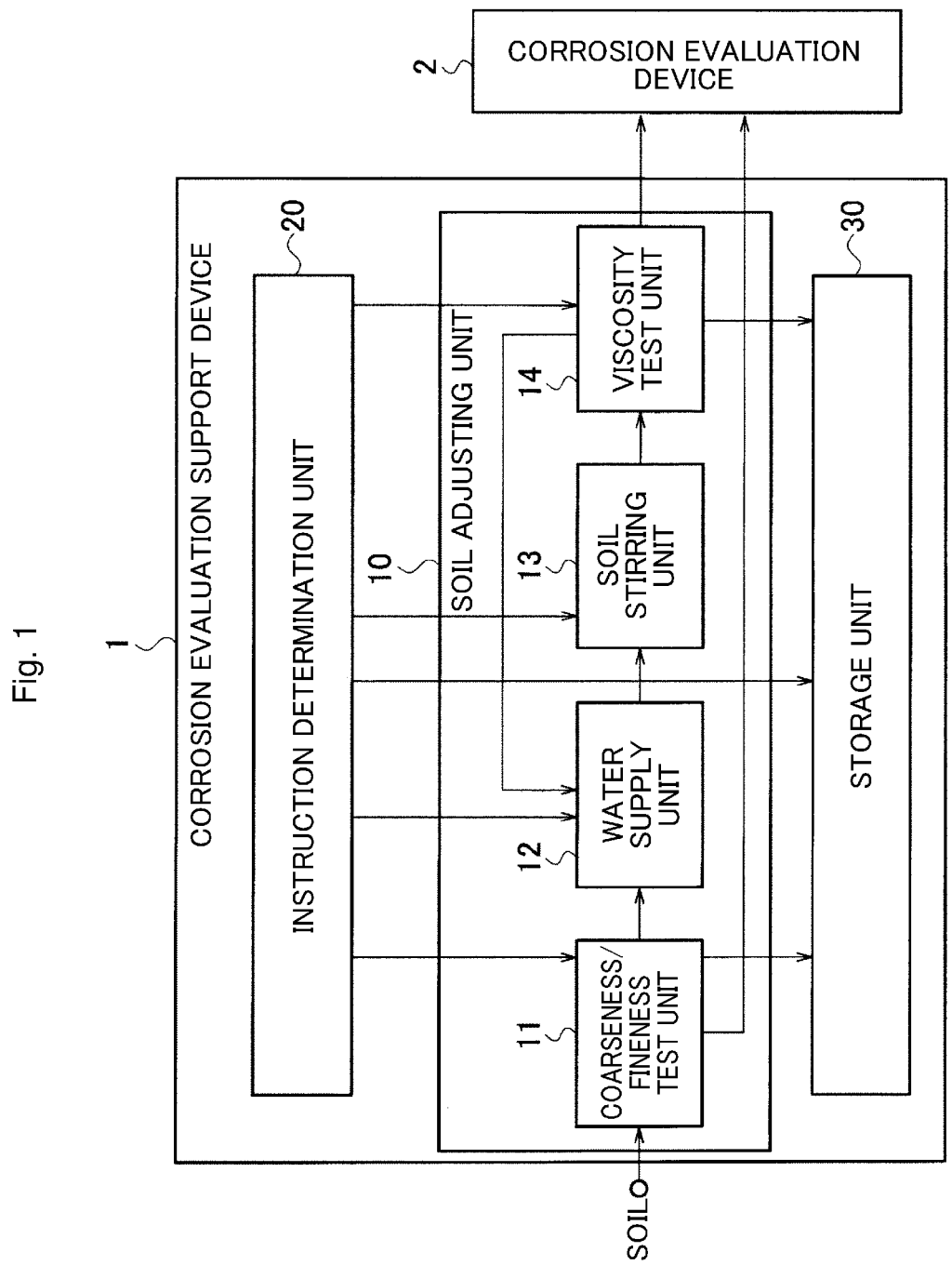
FIG. 1 is a functional block diagram schematically showing a configuration of a corrosion evaluation support device according to a first embodiment.

FIG. 1 is a functional block diagram schematically showing a configuration of a corrosion evaluation support device for an embedded metallic material according to a first embodiment. The corrosion evaluation support device 1 for an embedded metallic material (hereinafter referred to as a "corrosion evaluation support device") adjusts soil in which metal is embedded to evaluate and measure corrosion of the metal embedded in the ground with good reproducibility. The adjusted soil is fed into a corrosion evaluation device 2. The corrosion evaluation device 2 evaluates corrosion of the metal by performing electrochemical measurement. In the present embodiment, the corrosion evaluation device 2 can measure corrosion of metal with good reproducibility and evaluate the corrosion with high accuracy by using soil adjusted by the corrosion evaluation support device 1.

The illustrated corrosion evaluation support device 1 includes a corrosion soil adjusting unit 10, an instruction determination unit 20, and a storage unit 30. The soil adjusting unit 10 includes a coarseness/fineness test unit 11, a water supply unit 12, a soil stirring unit 13, and a viscosity test unit 14.

The coarseness/fineness test unit 11 analyzes soil particles of soil that is used to evaluate corrosion of an embedded metallic material. Specifically, the coarseness/fineness test unit 11 carries out a test for determining whether or not soil introduced into the corrosion evaluation support device 1 is sticky soil. According to an engineering classification method for soil (JGS0051) defined in the Japanese geotechnical society standards, classes are defined based on the size of soil particles constituting soil, and soil that is constituted by soil particles of 5 µm or less is called "clay", soil that is constituted by soil particles of 5 to 75 µm is called "silt", soil that is constituted by soil particles of 75 µm to 2 mm is called "sand", and soil that is constituted by soil particles of 2 mm or more is called "gravel". Out of these, clay and silt are classified as a fine grain fraction, and sand and gravel are classified as a coarse grain fraction. From an engineering standpoint, soil that contains the fine grain fraction in an amount of 50% or more is determined as being sticky soil. In the present embodiment, whether or not target soil is sticky soil may also be determined using an engineering determination method like this, for example.

In this case, the coarseness/fineness test unit 11 measures a particle size distribution and stores the result of measurement in the storage unit 30, and the instruction determination unit 20 makes a determination using the result of measurement stored in the storage unit 30. As a specific method for measuring the particle size distribution, it is possible to use the test method for particle size distribution of soils described in JIS A 1204:2009 or a laser diffraction/scattering particle size analysis method, for example.

However, in the test method for particle size distribution of soils described in JIS, it is necessary to apply sieve analysis to particles of 75 µm or more and apply sedimentation analysis to particles smaller than 75 µm, and it takes a long time until a result is obtained, and more than 500 mL of a soil sample is required for the analysis. In the laser diffraction/scattering particle size analysis method, the time it takes for the measurement is a few tens of seconds, which is very short, and only a few milliliters of a soil sample is required for the analysis. For the reasons described above, it is preferable to use the laser diffraction/scattering particle size analysis method in the measurement performed by the coarseness/fineness test unit 11.

Note that, if the range of the particle size distribution of a soil sample is wide and the soil sample is not sufficiently mixed, there may be cases where a correct result cannot be obtained using the laser diffraction/scattering particle size analysis method, depending on a sampling method of the soil. Therefore, it is preferable to obtain a plurality of soil samples from a sufficiently mixed soil sample, and take an average of measurement results of these soil samples to be a final measurement result.

Figure 2:
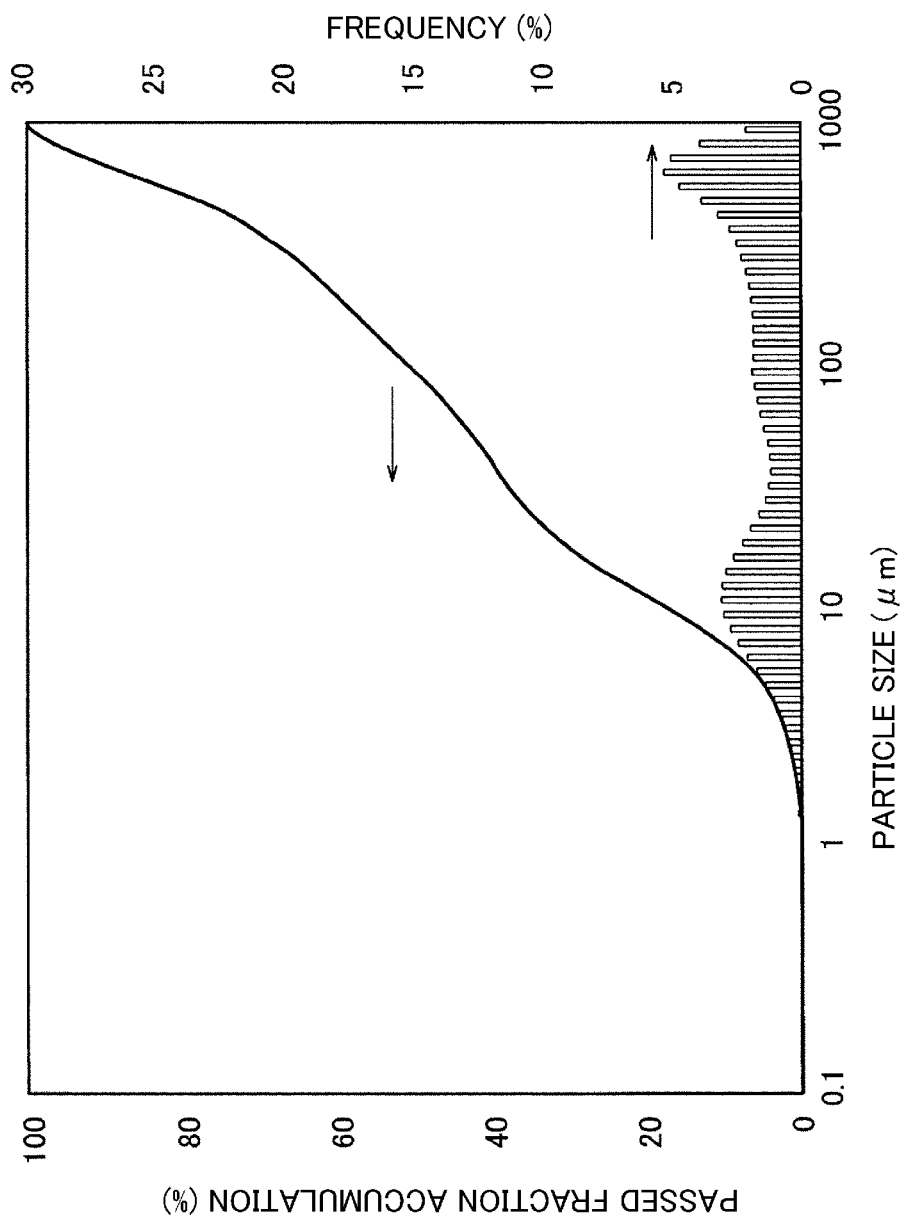
FIG. 2 is a diagram showing an example of a measurement result for which it was determined that soil was not sticky soil.
Figure 3:
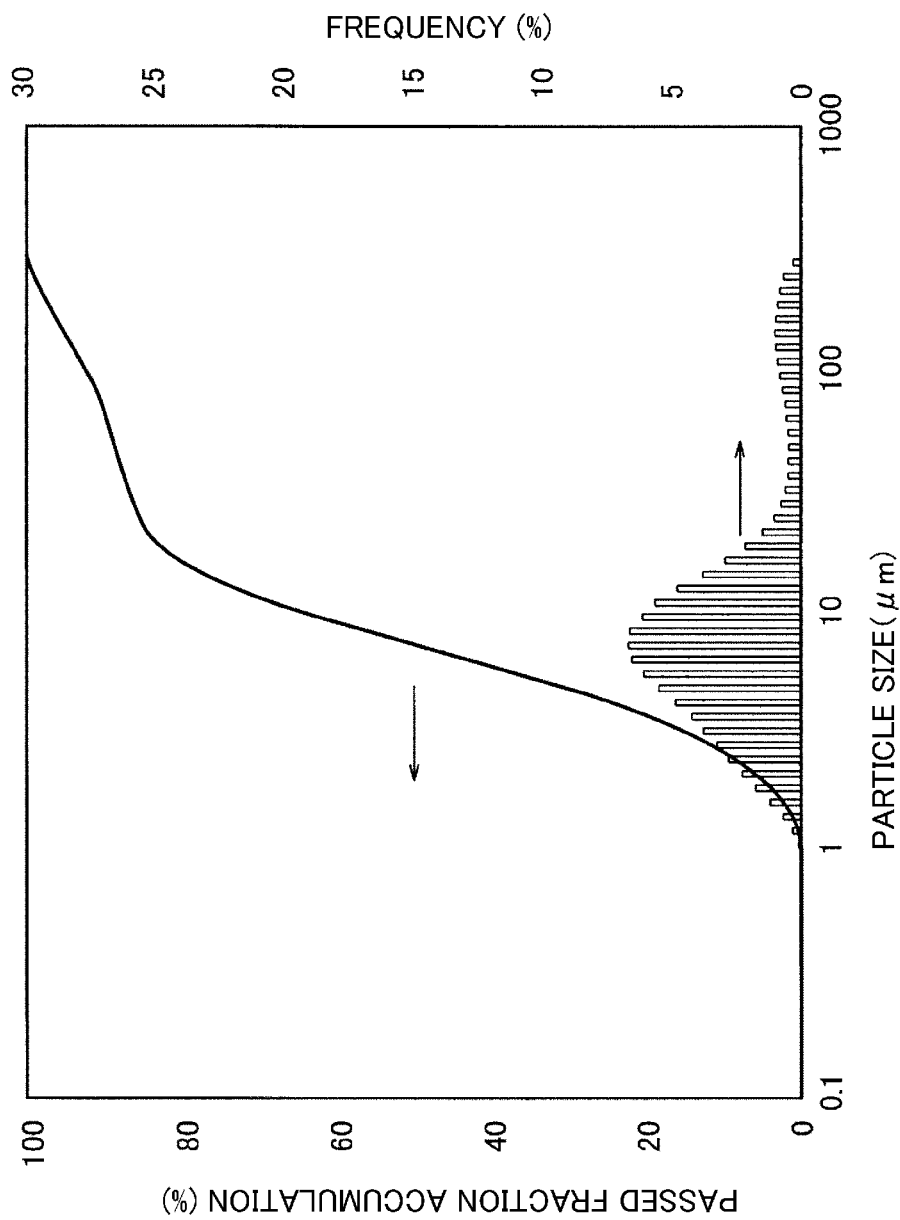
FIG. 3 is a diagram showing an example of a measurement result for which it was determined that soil was sticky soil.

FIGS. 2 and 3 show example measurement results of the particle size distribution measured by the coarseness/fineness analysis unit 11. In FIGS. 2 and 3, passed fraction accumulation (%) on the left vertical axis corresponds to a curved graph and frequency (%) on the right vertical axis corresponds to a bar graph. FIG. 2 shows a measurement result of soil that was determined as not being sticky soil, and the amount of the fine grain fraction is less than 50%. FIG. 3 shows a measurement result of soil that was determined as being sticky soil, and the amount of the fine grain fraction is greater than or equal to 50%.

If it is determined that the soil is sticky soil, the soil is transferred to (fed into) the water supply unit 12. If it is determined that the soil is not sticky soil, adjustment of the soil is unnecessary, and therefore the soil is fed into the corrosion evaluation device 2 without passing through the water supply unit 12, the soil stirring unit 13, and the viscosity test unit 14.

The water supply unit 12 supplies water to the soil following an instruction from the instruction determination unit 20. Upon determining that the soil is sticky soil, the instruction determination unit 20 instructs the water supply unit 12 to supply water. At this time, the instruction determination unit 20 may also specify a water supply amount in the instruction given to the water supply unit 12. Although the water supply amount may be set to a suitable amount, the proportion of a solid phase in soil is 50%, the proportion of a liquid phase and a gas phase is 50%, and respective proportions of the liquid phase and the gas phase compete with each other, and therefore water may be supplied such that the liquid phase accounts for 80% of a total amount of the liquid phase and the gas phase. That is, water may be supplied such that the volume water content in the introduced soil becomes 40%. Note that, if the soil has been determined as not being in a liquid state by the viscosity test unit 14 and has been returned to the water supply unit 12 again, the soil contains a certain amount of previously supplied water, and therefore the water supply unit 12 may supply water in an amount of 5% of the volume of the soil, following an instruction from the instruction determination unit 20, and transfer the soil to the soil stirring unit 13. The water-containing soil supplied with water is transferred to (fed into) the soil stirring unit 13.

Water supplied by the water supply unit 12 may be pure water, but it is preferable to use soil water that is extracted from the soil to be used. Chemical components contained in the soil are one of environmental factors that affect corrosion of embedded metal. Accordingly, if pure water is supplied, there is a concern that corrosion may be underestimated as a result of chemical components in the soil flowing out into the water. If water extracted from the soil is used, chemical components in the soil are dissolved in the water in advance, and therefore, from the standpoint of chemical equilibrium, it can be expected that unplanned effluence of the chemical components from the evaluation target soil can be suppressed.

The soil stirring unit 13 stirs the soil supplied with water by the water supply unit 12, following an instruction from the instruction determination unit 20. Depending on the soil, firm lumps called "dama" may be formed in the soil. Therefore, the soil is stirred by the soil stirring unit 13 until water supplied by the water supply unit 12 uniformly spreads throughout the soil and all lumps in the soil disappear. Note that the instruction determination unit 20 may make a determination to end the step performed by the soil stirring unit 13 by using an image recognition technology, for example. Alternatively, optimum conditions may be determined in advance through preliminary examination and consideration of a stirring speed and a stirring time at which lumps in the soil completely disappear, and the instruction determination unit 20 may make the determination to end the step based on the optimum conditions and give an instruction to the soil stirring unit 13. The stirred soil is transferred to (fed into) the viscosity test unit 14.

Note that the number of times of stirring and a stirring force are preferably set such that soil particles will not collapse. Whether or not soil particles have collapsed may be determined by measuring a particle size distribution as described above regarding the coarseness/fineness test unit 11, for example. If particle distribution curves that are obtained by measuring the particle size distribution before and after the stirring performed by the soil stirring unit 13 have the same shape, it can be determined that soil particles have not collapsed.

There is no limitation on the method for stirring soil by the soil stirring unit 13 so long as water supplied by the water supply unit 12 uniformly spreads throughout the soil and all lumps in the soil disappear. For example, the soil may be stirred by moving two rod-like objects in a circular path or using a mechanism similar to that of an automatic stirrer that is used in a food plant or the like. However, it is preferable to use a material that is hard to rust, such as a stainless steel or plastic as the material of the stirrer.

The viscosity test unit 14 measures fluidity of the stirred water-containing soil, following an instruction from the instruction determination unit 20. Here, the viscosity test unit 14 carries out a viscosity test as the measurement of fluidity. A soil consistency test may be used as the method of the viscosity test of soil, for example.

Figure 4:
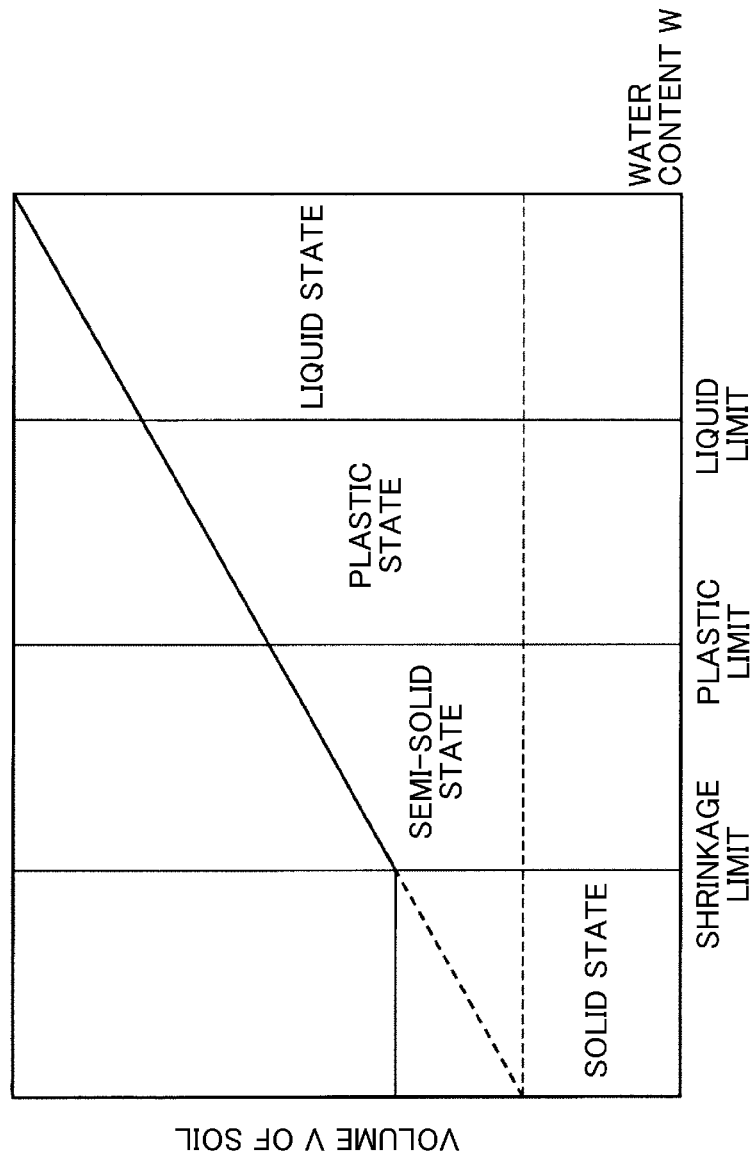
FIG. 4 is a diagram showing soil states that change according to the water content.

FIG. 4 is a diagram showing soil states that change according to the water content. The state of soil particles changes according to the water content in the order of a solid state, a semi-solid state, a plastic state, and a liquid state. Magnitudes of soil resistance that change along with this state change are collectively called "consistency". Note that a boundary between the solid state and the semi-solid state is called a "shrinkage limit", a boundary between the semi-solid state and the plastic state is called a "plastic limit", and a boundary between the plastic state and the liquid state is called a "liquid limit".

In order to establish an evaluation system with which corrosion of an embedded metallic material can be correctly evaluated even if any type of soil is used, it is preferable that soil can be uniformly held in a container. That is, the soil held in the container is preferably in the liquid state. Therefore, in the present embodiment, whether or not the soil is in the liquid state is determined. If the soil is in the liquid state, the soil has fluidity and can be uniformly held in the container.

The viscosity test may be carried out using the test method for liquid limit of soils described in JIS A 1205, for example. In the test method for liquid limit, soil is uniformly kneaded, a brass pan in which the soil is placed is dropped from a height of 1 cm at a rate of two times per second, and the number of times of dropping at which two halved portions of the soil divided by a groove join over a length of 1.5 cm in a bottom portion of the groove is measured, and if the number of times of dropping is 25, it is determined that the soil is in the state of the liquid limit.

Accordingly, the viscosity test unit 14 carries out a liquid limit test to measure the number of times of dropping described above, and stores the number of times of dropping in the storage unit 30. The instruction determination unit 20 determines whether or not the soil is in the liquid state by using the number of times of dropping (result of measurement) stored in the storage unit 30. Here, if the number of times of dropping is no greater than 25, the instruction determination unit 20 determines that the soil is in the liquid state and ends the step performed by the soil adjusting unit 10. If the soil is determined as being in the liquid state, adjustment of the soil is complete, and the soil is fed into the corrosion evaluation device 2 and used to evaluate corrosion of embedded metal.

On the other hand, if the number of times of dropping is more than 25 (26 or more), the viscosity test unit 14 may determine that the soil is not in the liquid state and return the soil to the water supply unit 12. That is, the instruction determination unit 20 may cause the water supply unit 12, the soil stirring unit 13, and the viscosity test unit 14 to repeatedly perform water supply, stirring, and measurement of fluidity until the stirred soil is determined as being in the liquid state.

Note that the viscosity test unit 14 may also carry out a direct box shear test, a uniaxial compressive strength test, a triaxial compressive strength test, or the like for evaluating resistance to sliding, as a method of the viscosity test. "Strength" that is a dynamic property of soil is described as a sum of an internal frictional angle and an adhesiveness. The instruction determination unit 20 may calculate an adhesiveness through these tests by using Coulomb's empirical formula, and determine that the soil is in the liquid state if the adhesiveness is no greater than a predetermined value.

Upon determining that the soil is sticky soil based on the result of analysis performed by the coarseness/fineness test unit 11, the instruction determination unit 20 (a first determination unit, a second determination unit) continues the step performed by the soil adjusting unit 10 and outputs a water supply instruction in which a water supply amount is specified to the water supply unit 12. Also, based on the result of measurement performed by the viscosity test unit 14, the instruction determination unit 20 gives an instruction and makes a determination to end the step performed by the soil adjusting unit 10 or return the soil to the water supply unit 12, for example.

Specifically, the instruction determination unit 20 determines whether or not the soil is sticky soil by using the result of analysis performed by the coarseness/fineness test unit 11, and upon determining that the soil is sticky soil, transfers the soil to the water supply unit 12. Also, the instruction determination unit 20 determines whether or not the stirred soil is in the liquid state by using the result of measurement of fluidity performed by the viscosity test unit 14, and causes the water supply unit 12, the soil stirring unit 13, and the viscosity test unit 14 to repeatedly perform water supply, stirring, and measurement of fluidity until the soil is determined as being in the liquid state.

The result of analysis performed by the coarseness/fineness test unit 11 and the result of measurement of fluidity performed by the viscosity test unit 14 are stored in the storage unit 30. If a particle size distribution has been measured by the coarseness/fineness test unit 11, for example, the instruction determination unit 20 calculates a blend ratio between clay, silt, and sand from a particle distribution curve stored in the storage unit 30. Also, if a triaxial compression test has been carried out by the viscosity test unit 14, for example, the instruction determination unit 20 calculate an adhesiveness from a measurement result and Coulomb's empirical formula.

Figure 5:
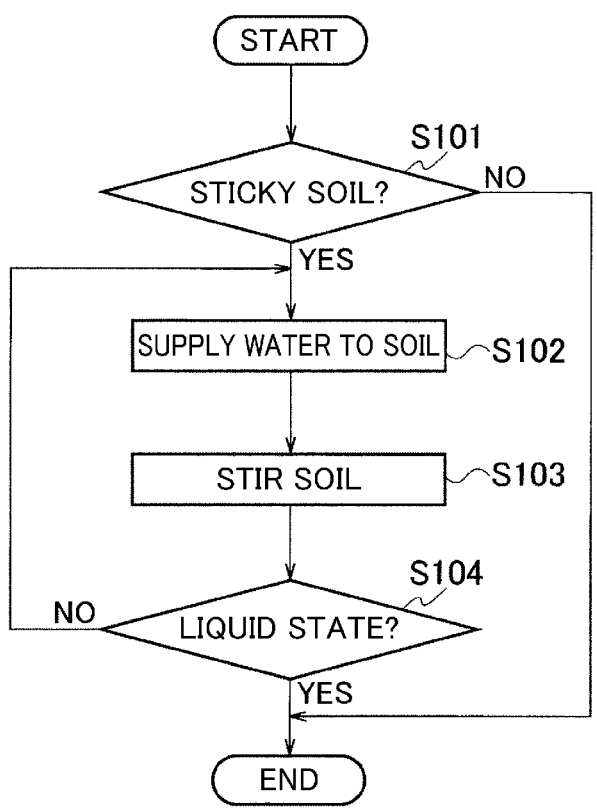
FIG. 5 is an operation flow showing a procedure of processing performed by the corrosion evaluation support device.

FIG. 5 is an operation flow showing a processing procedure of a corrosion evaluation support method performed by the corrosion evaluation support device according to the present embodiment.

As shown in FIG. 5, first, soil is introduced into the corrosion evaluation support device 1, the coarseness/fineness test unit 11 analyzes soil particles of the soil, and the instruction determination unit 20 determines whether or not the soil is sticky soil based on the result of analysis (step S101). If it is determined that the soil is not sticky soil (step S101: NO), adjustment of the soil is considered as being unnecessary, and the operation flow ends.

If it is determined that the soil is sticky soil (step S101: YES), the soil is transferred to the water supply unit 12, and the water supply unit 12 supplies water to the soil (step S102). Thereafter, the water-containing soil is transferred to the soil stirring unit 13, and the soil stirring unit 13 stirs the soil until the state of the soil becomes uniform (step S103). Thereafter, the stirred water-containing soil is transferred to the viscosity test unit 14, the viscosity test unit 14 measures fluidity of the soil, and the instruction determination unit 20 determines whether or not the soil is in the liquid state based on the result of measurement (step S104). If it is determined that the soil is not in the liquid state, the procedure returns to step S102 and step S102 and the following steps are repeatedly performed. If it is determined that the soil is in the liquid state, the processing flow ends.

The corrosion evaluation support device 1 according to the embodiment described above includes the coarseness/fineness test unit 11 that analyzes soil particles of soil that is used to evaluate corrosion of an embedded metallic material, the water supply unit 12 that supplies water to the soil, the soil stirring unit 13 that stirs the soil supplied with water, and the viscosity test unit 14 that measures fluidity of the stirred soil.

With this configuration, the present embodiment can support evaluation of corrosion of metal embedded in the ground such that the corrosion can be evaluated with high accuracy even if any type of soil is used. Specifically, even if the soil (sample soil) that is used to evaluate corrosion of the embedded metallic material is sticky soil, if the soil is adjusted to the liquid state by using the corrosion evaluation support device 1 according to the present embodiment, it is possible to easily fill a container with the soil without forming a gap and easily make the state of an interface between metal (electrode) and soil particles every time the same (i.e., embed the metal in the soil under the same conditions) in electrochemical measurement. As a result, according to the present embodiment, reproducibility of measurement data obtained in the electrochemical measurement can be assured, and corrosion of the metal embedded in the ground can be evaluated with high accuracy.

Second Embodiment

Figure 6:
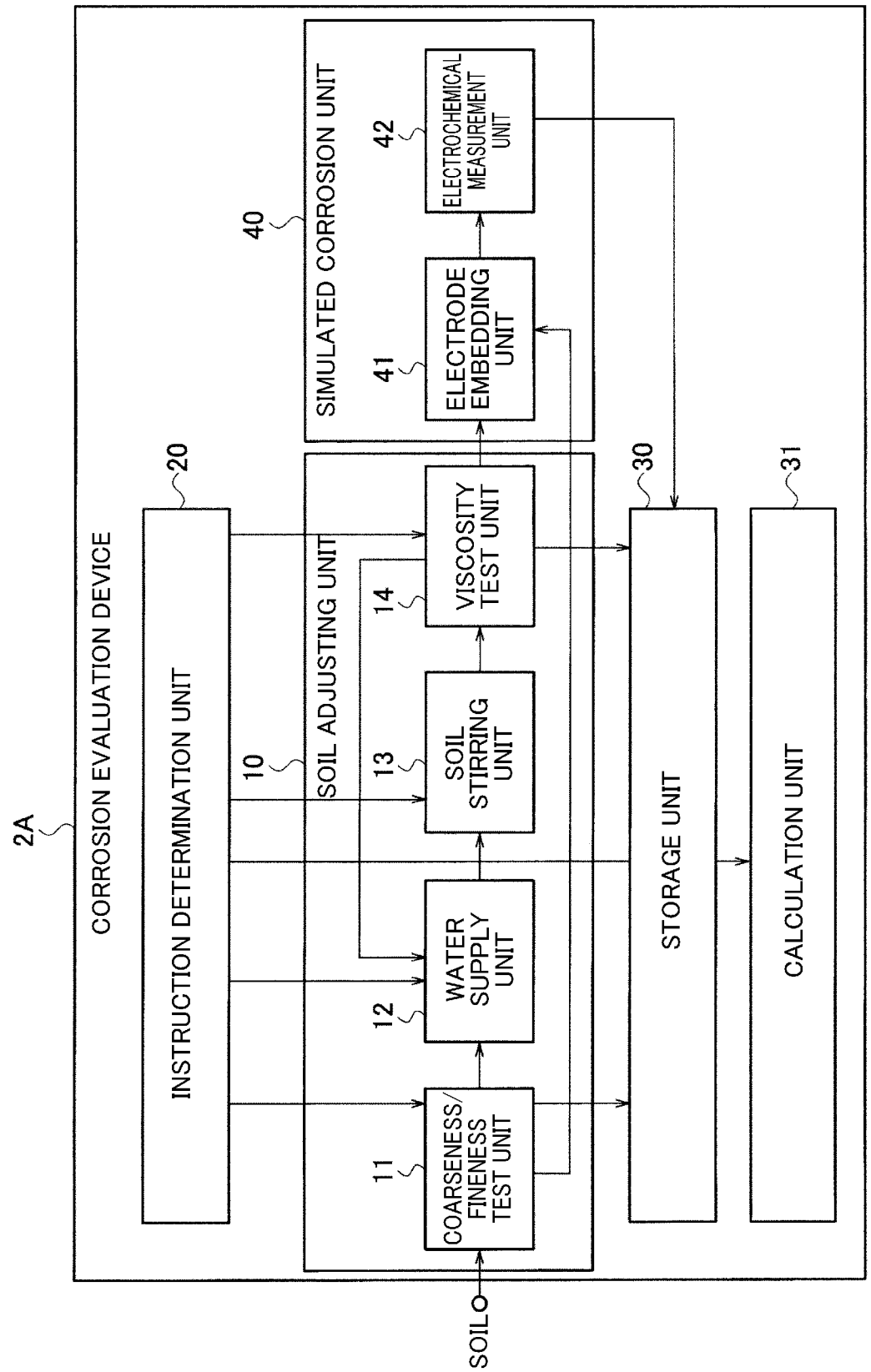
FIG. 6 is a functional block diagram schematically showing a configuration of a corrosion evaluation device according to a second embodiment.

FIG. 6 is a functional block diagram schematically showing a configuration of a corrosion evaluation device 2A (corrosion evaluation system) for an embedded metallic material according to a second embodiment of the present invention. The corrosion evaluation device 2A according to the present embodiment is obtained by providing the corrosion evaluation support device 1 according to the first embodiment with a simulated corrosion unit 40 for evaluating corrosion of metal and a calculation unit 31. The corrosion evaluation device 2 according to the present embodiment has a mechanism in which soil adjusted by the soil adjusting unit 10 is transferred to the simulated corrosion unit 40 and corrosion of an embedded metallic material can be evaluated using the soil.

The illustrated simulated corrosion unit 40 includes an electrode embedding unit 41 and an electrochemical measurement unit 42. The electrode embedding unit 41 includes soil that has passed through the soil adjusting unit 10 and an electrode that is constituted by a metallic material that is an evaluation target, the soil and the electrode being held in a container. Details of the configuration of the electrode vary depending on the method of electrochemical measurement performed by the electrochemical measurement unit 42.

If a two-electrode method is used, for example, the number of electrodes is two, and the electrodes are constituted by a working electrode and a counter electrode.

Note that the same material as the embedded metallic material of which a corrosion amount is to be estimated is used as the working electrode and the counter electrode. If a three-electrode method is used, the number of electrodes is three, and the electrodes are constituted by a working electrode, a counter electrode, and a reference electrode. Note that the same material as the embedded metallic material of which a corrosion amount is to be estimated is used as the working electrode, and either of platinum and carbon, which are commonly used, may be used as the counter electrode, and either of a silver-silver chloride electrode and a calomel electrode, which are commonly used, may be used as the reference electrode, for example.

The electrochemical measurement unit 42 performs electrochemical measurement to calculate a corrosion rate. In a case where the corrosion rate is electrochemically calculated, a method of measuring a reaction resistance (charge transfer resistance $R_{ct}$) that occurs along with progress of corrosion is commonly used (see NPL 1). As an electrochemical method, a direct current polarization resistance method or an alternating current impedance method is used, for example.

In measurement performed in the direct current polarization resistance method, direct current potential sweeping is performed relative to a natural potential in a range where the metal surface is not roughened and a resistance value can be calculated from an obtained current-potential characteristic. For example, the electrochemical measurement may be performed with an applied potential of ±5 [mV], which is an applied potential in the alternating current impedance method of which influence on the metal surface is considered as being small. The charge transfer resistance $R_{ct}$ is calculated from an inclination of the obtained current-potential characteristic. The inclination may be calculated using the least squares method or an extrapolation method, for example.

In the alternating current impedance method, measurement is performed from a high frequency toward a low frequency, and arcs appear in a high frequency range and a low frequency range, respectively. Since the charge transfer resistance $R_{ct}$ is considered as being derived from the arc in the low frequency range, the charge transfer resistance $R_{ct}$ is calculated from values on the horizontal axis (impedance real part, Z' [Ω·cm²]) from the start point to the end point of the arc in the low frequency range. The measurement is preferably performed with an alternating current applied potential of ±5 [mV] of which influence on the metal surface is considered as being small.

Note that the charge transfer resistance $R_{ct}$ obtained in the direct current polarization measurement is calculated as a resistance value of the entire measurement system, and therefore a soil resistance value that is too large to ignore relative to the charge transfer resistance $R_{ct}$ may appear in the measurement performed in the soil sample. On the other hand, in the alternating current impedance method, measured resistance values can be separated based on the frequency of the applied potential, and the arc in the high frequency range reflects resistance derived from the soil and the art in the low frequency range only reflects the charge transfer resistance $R_{ct}$. Therefore, it is possible to accurately find only the charge transfer resistance $R_{ct}$ using the alternating current impedance method. For the reasons described above, it is preferable to use the alternating current impedance method in the electrochemical measurement unit 42.

The electrochemical measurement unit 42 stores the charge transfer resistance $R_{ct}$, which is the result of measurement, in the storage unit 30. The calculation unit 31 calculates a corrosion current density $i_{corr}$ from the charge transfer resistance $R_{ct}$ stored in the storage unit 30 based on the following formula.

Math 1

$$i_{corr} = K \cdot \frac{1}{R_{ct}} \quad (1)$$

Here, $i_{corr}$ represents the corrosion current density [A/cm$^2$], K represents a conversion factor [V], and $R_{ct}$ represents the charge transfer resistance [Ω·cm$^2$]. The conversion factor K is calculated in advance. That is, the conversion factor K is calculated based on the following formula by finding a Tafel slope from an anodic polarization curve and a cathodic polarization curve.

Math 2

$$K = \frac{\beta_a \cdot \beta_c}{2.3(\beta_a + \beta_c)} \quad (2)$$

Here, $\beta_a$ represents an anodic slope [V/decade] and $\beta_c$ represents a cathodic slope [V/decade]. Alternatively, the conversion factor K may be calculated assuming that $\beta_a = \beta_c = 0.1$ [V/decade] without measuring the Tafel slope.

Next, the calculation unit 31 calculates the corrosion rate r based on the following formula.

Math 3

$$r = \frac{M}{z\rho F} \cdot i_{coor} \quad (3)$$

Here, r represents the corrosion rate [cm/sec], z represents an ionic valence, ρ represents a density [g/cm$^2$], F represents the Faraday constant [C], and M represents an atomic weight [g/mol].

The corrosion evaluation device 2A according to the present embodiment described above is obtained by providing the corrosion evaluation support device 1 according to the first embodiment with the simulated corrosion unit 40 for evaluating corrosion of metal. Accordingly, in the present embodiment, soil adjusted by the soil adjusting unit 10 is used in the electrochemical measurement, and therefore corrosion of metal embedded in the ground can be evaluated with high accuracy even if any type of soil is used.

Note that a general-purpose computer system that includes, for example, a CPU (Central Processing Unit, processor), a memory, a storage (HDD: Hard Disk Drive, SSD: Solid State Drive), a communication device, an input device, and an output device can be used as the instruction determination unit 20 and the calculation unit 31 of the corrosion evaluation support device 1 and the corrosion evaluation device 2A described above. Functions of the instruction determination unit 20 and the calculation unit 31 are realized as a result of the CPU executing a program for the instruction determination unit 20 and the calculation unit 31 that is loaded on the memory in the computer system. The program for the instruction determination unit 20 and the calculation unit 31 may also be stored in a computer-readable recording medium such as an HDD, an SSD, a USB memory, a CD-ROM, a DVD-ROM, or an MO, or may also be distributed via a network.

Note that the present invention is not limited to the embodiment described above, and many changes can be made within the scope of the gist of the present invention.

REFERENCE SIGNS LIST

1 Corrosion evaluation support device
2, 2A Corrosion evaluation device
10 Soil adjusting unit
11 Coarseness/fineness test unit
12 Water supply unit
13 Soil stirring unit
14 Viscosity test unit
20 Instruction determination unit
30 Storage unit
31 Calculation unit
40 Simulated corrosion unit
41 Electrode embedding unit
42 Electrochemical measurement unit

The invention claimed is:

1. A corrosion evaluation support device comprising:
a coarseness/fineness test unit configured to analyze soil particles of soil that is used to evaluate corrosion of an embedded metallic material, the coarseness/fineness test unit comprising a laser that is configured to perform a laser diffraction/scattering particle size analysis;
a water supply unit configured to supply water to the soil;
a soil stirring unit configured to stir the soil supplied with water; and
a viscosity test unit comprising sensor that is configured to measure fluidity of the stirred soil.

2. The corrosion evaluation support device according to claim 1, further comprising a first instruction determination unit comprising a processor configured to determine whether or not the soil is sticky soil by using a result of analysis of the soil particles, wherein the first instruction determination unit transfers the soil to the water supply unit upon determining that the soil is sticky soil.

3. The corrosion evaluation support device according to claim 2, further comprising a second instruction determination unit comprising a processor that is configured to determine whether or not the stirred soil is in a liquid state by using a result of measurement of the fluidity, wherein the second instruction determination unit causes the water supply unit, the soil stirring unit, and the viscosity test unit to repeatedly perform water supply, stirring, and measurement of fluidity until the stirred soil is determined as being in the liquid state.

4. The corrosion evaluation support device according to claim 2, wherein soil water that is extracted from the soil is used as the water.

5. The corrosion evaluation support device according to claim 1, further comprising an instruction determination unit configured to determine whether or not the stirred soil is in a liquid state by using a result of measurement of the fluidity, wherein the instruction determination unit causes the water supply unit, the soil stirring unit, and the viscosity test unit to repeatedly perform water supply, stirring, and measurement of fluidity until the stirred soil is determined as being in the liquid state.

6. The corrosion evaluation support device according to claim 5, wherein soil water extracted from the soil is used as the water.

7. The corrosion evaluation support device according to claim 1, wherein soil water extracted from the soil is used as the water.

8. A corrosion evaluation support method to be carried out by a corrosion evaluation support device, the method comprising:
an analysis step of analyzing soil particles of soil that is used to evaluate corrosion of an embedded metallic material, the analysis step being performed by a laser using a laser diffraction/scattering particle size analysis method;
a water supply step of supplying water to the soil;
a stirring step of stirring the soil supplied with water; and
a measurement step of measuring fluidity of the stirred soil.

9. The corrosion evaluation support method according to claim 8, further comprising a first instruction determination step of determining whether or not the soil is sticky soil by using a result of analysis of the soil particles.

10. The corrosion evaluation support method according to claim 6, further comprising a second instruction determination step of determining whether or not the stirred soil is in a liquid state by using a result of measurement of the fluidity, wherein the water supply step, the stirring step, and the measurement step are repeatedly performed until the stirred soil is determined as being in the liquid state.

11. The corrosion evaluation support method according to claim 9, wherein soil water extracted from the soil is used as the water.

12. The corrosion evaluation support method according to claim 8, further comprising an instruction determination step of determining whether or not the stirred soil is in a liquid state by using a result of measurement of the fluidity, wherein the water supply step, the stirring step, and the measurement step are repeatedly performed until the stirred soil is determined as being in the liquid state.

13. The corrosion evaluation support method according to claim 12, wherein soil water extracted from the soil is used as the water.

14. The corrosion evaluation support method according to claim 8, wherein soil water extracted from the soil is used as the water.

* * * * *